United States Patent [19]

Hoffmann et al.

[11] 4,055,571
[45] Oct. 25, 1977

[54] O-[1-ALKYL-5-SUBSTITUTED-MERCAPTO-TRIAZOL(3)YL]-PHOSPHORIC(PHOSPHONIC) ACID ESTERS AND ESTER-AMIDES

[75] Inventors: Hellmut Hoffmann, Wuppertal; Ingeborg Hammann, Cologne; Wilhelm Stendel, Wuppertal, all of Germany

[73] Assignee: Bayer Aktiengesellschaft, Leverkusen, Germany

[21] Appl. No.: 573,203

[22] Filed: Apr. 30, 1975

[30] Foreign Application Priority Data

May 16, 1974  Germany .............................. 2423765

[51] Int. Cl.² .......................................... C07D 249/12
[52] U.S. Cl. .................................. 260/308 R; 560/148; 560/159; 424/200
[58] Field of Search ........................ 260/308, 308 R; 424/200

[56] References Cited

U.S. PATENT DOCUMENTS

| | | | |
|---|---|---|---|
| 2,754,244 | 7/1956 | Gysin et al. | 260/310 R |
| 3,867,396 | 2/1975 | Dawes et al. | 260/308 R |
| 3,867,397 | 2/1975 | Dawes et al. | 260/308 R |
| 3,867,398 | 2/1975 | Bohner et al. | 260/308 R |
| 3,888,874 | 6/1975 | Dawes et al. | 260/308 R |

FOREIGN PATENT DOCUMENTS

2,301,400  7/1974  Germany .......................... 260/308 R

*Primary Examiner*—Raymond V. Rush
*Attorney, Agent, or Firm*—Burgess, Dinklage & Sprung

[57] ABSTRACT

O-Alkyl-O-[1-alkyl-5-substituted-mercapto-triazol(-3)yl]-phosphoric(phosphonic) acid esters and esteramides of the formula

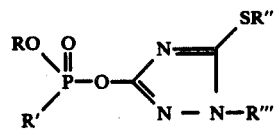

in which
R is alkyl with 1 to 6 carbon atoms,
R' is alkyl, alkoxy, monoalkylamino or dialkylamino, each with up to 6 carbon atoms, or phenyl,
R" is cyanoalkyl with 1 to 4 carbon atoms or alkenyl with 2 to 6 carbon atoms or, in the case where R' is alkylamino, may also be alkyl with 1 to 4 carbon atoms, and
R''' is alkyl with 1 to 4 carbon atoms, which possess insecticidal and acaricidal properties.

1 Claim, No Drawings

O-[1-ALKYL-5-SUBSTITUTED-MERCAPTO-TRIAZOL(3)YL]-PHOSPHORIC(PHOSPHONIC) ACID ESTERS AND ESTER-AMIDES

The present invention relates to and has for its objects the provision of particular new O-alkyl-O-[1-alkyl-5-substituted-mercapto-triazol(3)yl]-phosphoric(phosphonic) acid esters and ester-amides which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. No. 2,754,244 and German published specification Dos No. 2,259,960 that certain pyrazolylthiono-phosphoric acid esters, for example, O,O-dimethyl-(Compound A) and O,O-diethyl-O-[3-methylpyrazol(5)yl]-thionophosphoric acid esters (Compound B), and certain triazolylthionophosphonic acid esters, for example O-ethyl-O-[1-isopropyl-5-methylthio-1,2,4-triazol-(3)yl]-thionophenylphosphonic acid ester (Compound C), possess insecticidal and acaricidal properties.

The present invention provides, as new compounds, the O-triazolylphosphoric(phosphonic) acid esters and esteramides of the general formula

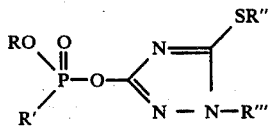

(I)

in which
R is alkyl with 1 to 6 carbon atoms,
R' is alkyl, alkoxy, monoalkylamino or dialkylamino, each with up to 6 carbon atoms, or phenyl,
R'' is cyanoalkyl with 1 to 4 carbon atoms or alkenyl with 2 to 6 carbon atoms or, in the case where R' is alkylamino, may also be alkyl with 1 to 4 carbon atoms, and
R''' is alkyl with 1 to 4 carbon atoms.

Preferably, R is straight-chain or branched alkyl with 1 to 4 carbon atoms, R' is straight-chain or branched alkyl, alkoxy, monoalkylamino or dialkylamino, each with up to 4 carbon atoms, or phenyl, R'' is alkenyl with 3 or 4 carbon atoms, cyanomethyl, 1-cyanoethyl or 2-cyanoethyl, or, when R' is alkylamino, one of the foregoing or straight-chain or branched alkyl with 1 to 3 carbon atoms, and R''' is straight-chain or branched alkyl with 1 to 3 carbon atoms.

Surprisingly, the O-triazolylphosphoric(phosphonic) acid esters and ester-amides according to the invention show a better insecticidal and acaricidal action than previously known compounds of analogous structure and of the same type of action. The new products can not only be employed against insects and mites which damage plants, but also against pests harmful to health and pests of stored products as well as in the veterinary medicine field, against animal ectoparasites, such as, for example, parasitic fly larvae. They thus represent a genuine enrichment of the art.

The invention also provides a process for the preparation of an O-triazolylphosphoric(phosphonic) acid ester or ester-amide of the formula (I), in which a phosphoric(phosphonic) acid ester halide or ester-amide halide of the general formula

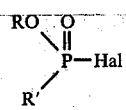

(II), in which
R and R' have the above-mentioned meanings, and
Hal is halogen, preferably chlorine, is reacted with a triazolyl derivative of the general formula

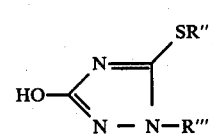

(III), in which
R'' and R''' have the above-mentioned meanings, the triazolyl derivative being reacted in the presence of an acid acceptor or in the form of an alkali metal salt, alkaline earth metal salt or ammonium salt, if appropriate in the presence of a solvent or diluent.

If, for example, O-ethyl-N-methyl-phosphoric acid ester-amide chloride and 1-methyl-3-hydroxy-5-ethyl-thiotriazole-(1,2,4) are used as starting materials, the course of the reaction can be represented by the following equation:

(IIa)

(IIIa)

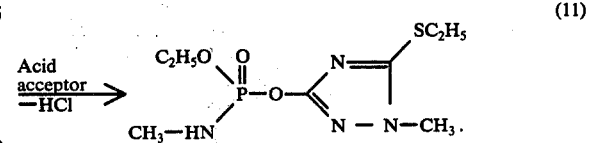

(II)

The phosphoric(phosphonic) acid derivatives (II) to be used as starting materials are known from the literature and can be prepared according to customary methods. The following may be mentioned as examples of these compounds: O,O-dimethyl-, O,O-diethyl-, O,O-di-n-propyl-, O,O-di-isopropyl-, O,O-di-n-butyl-, O,O-di-isobutyl-, O,O-di-sec.-butyl-, O,O-di-tert.-butyl-, O-ethyl-O-n-propyl-, O-ethyl-O-isopropyl-, O-n-butyl-O-ethyl-, O-ethyl-O-sec.-butyl- and O-ethyl-O-methyl-phosphoric acid diester chloride; O-methyl-, O-ethyl-, O-n-propyl-, O-isopropyl-, O-n-butyl-, O-sec.-butyl-, O-isobutyl- and O-tert.-butyl- methane-, ethane-, n-propane-, isopropane-, n-butane-, isobutane-, sec.-butane, tert.-butane- and phenyl-phosphonic acid ester chloride; and O-methyl-N-methyl-, O-ethyl-N-methyl-, O-n-propyl-N-methyl-, O-isopropyl-N-methyl-, O-n-butyl-N-methyl-, O-sec.-butyl-N-methyl-, O-methyl-N-ethyl-, O-ethyl-N-ethyl-, O-n-propyl-N-ethyl-, O-isopropyl-N-ethyl-, O-n-butyl-N-ethyl-, O-sec.-butyl-N-ethyl-, O-methyl-N-n-propyl-, O-ethyl-N-n-propyl-, O-n-propyl-N-n-propyl-, O-n-propyl-N-n-butyl-, O-isopropyl-N-ethyl-, O-isopropyl-N-n-butyl- and O-tert.-butyl-N-ethyl-phosphoric acid ester-amide chloride and the corresponding dialkylamino compounds.

The triazole derivatives of the formula (III), some of which are new, can be prepared in accordance with customary processes, especially by the following methods.

a. The known thiosemicarbazide derivatives of the general formula

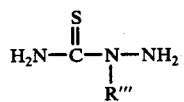

(IV), in which
R''' has the above-mentioned meaning,
are reacted, for example, with pyrocarbonic acid diethyl ester to give intermediates of the following general formula

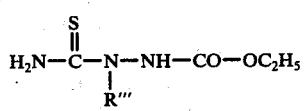

(V)

and these intermediates are then cyclized and reacted, for example in accordance with the following equation, with a compound of the formula R''Z wherein Z is an easily removed radical, for example halogen, and R'' has the meaning stated above:

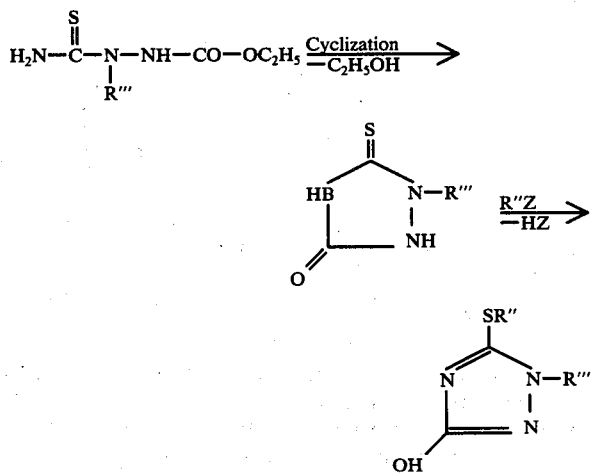

b. Carbonic acid alkyl ester hydrazides are reacted with aldehydes or ketones to give intermediates of the general formula

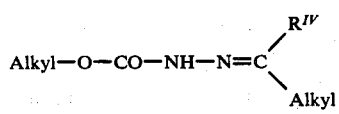

(VI), in which
$R^{IV}$ is hydrogen or alkyl, and thereafter the compound (VI) is reduced catalytically, allowed to react with thiocyanic acid, cyclized as mentioned under (a) in the presence of alcoholate and reacted further, as described, with a compound of the formula R''Z.

c. Alkylhydrazines are reacted with acetone and the resultant hydrazones are reacted with carbonic acid ethyl isothiocyanate to give the intermediates of the general formula

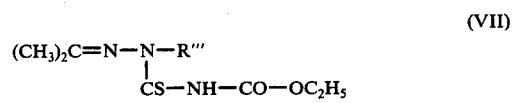

(VII)

and these are then directly cyclized in the presence of water and hydrochloric acid after which they are reacted, as has been described, with a compound R''Z.

The following may be mentioned as examples of triazolyl derivatives (III) to be reacted in accordance with the process: 1-methyl-, 1-ethyl-, 1-n-propyl- and 1-isopropyl-3-hydroxy-5-methylthiotriazole-(1,2,4) and the corresponding -5-ethylthio-, -5-n-propylthio-,-5-isopropylthio-, -5-allylthio-, -5-butenyl (2')thio-, -5-cyanomethylthio-, -5-(2'-cyanoethyl)-thio- and -5-(1'-cyanoethyl)-thio derivatives.

The preparative process is preferably carried out in the presence of a suitable solvent or diluent. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be employed as acid acceptors. Alkali metal carbonates and alkali metal alcoholates, such as sodium carbonate and potassium carbonate, sodium methylate and ethylate and potassium methylate and ethylate have proved particularly successful, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 100° C, preferably at from 35° to 60° C.

The reaction is in general allowed to take place under normal pressure.

To carry out the process, the starting materials are in general employed in equimolar ratios. An excess of one or other reactant in general produces no significant advantages. The reaction is preferably carried out in the presence of one the above-mentioned solvents, if appropriate in the presence of an acid acceptor, at the indicated temperatures. After a reaction time of one or more hours, in most cases at an elevated temperature, the batch is cooled, any solids which may be present are filtered off, the solvent is evaporated off in vacuo and the residue is taken up in an organic solvent, for example methylene chloride, or the reaction mixture is poured into water and extracted by shaking with an organic solvent, for example methylene chloride. The reaction mixture is then worked up in the usual manner by washing and drying the organic phase, evaporating the solvent and, if appropriate, distilling the residue.

Some of the new compounds are obtained in the form of oils which in most cases cannot be distilled without decomposition but can be freed from the last volatile constituents by so-called "slight distillation", that is to say by prolonged heating under reduced pressure to moderately elevated temperatures, and can be purified in this way. They are characterized by the refractive index.

As already mentioned, the O-trizolylphosphoric(-phosphonic) acid esters and ester-amides according to the invention are distinguished by an ooutstanding insecticidal and acaricidal activity. They are not only active against plant pests, pests harmful to health and pests of stored products, but also, in the veterinary medicine field, against animal parasites (ectoparasites), such as parasitic fly larvae. They couple a low phytotoxicity with a good action both against sucking and biting insects and against mites.

For this reason, the compounds according to the invention can be employed successfully as pesticides in plant protection as well as in the hygiene field, the field of protection of stored products and the veterinary field.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis,* and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus.*

In the case of the biting insects, above all there should be mentioned butterfly caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicase*), the small winter moth (*Cheimatobia brumata*), the green oak tortrix moth (*Tortrix Viridane*), the fall armyworm (*Laphygma frugiperda*) and cotton worm (*Prodenia litura*), the ermine moth (*Hyponomeuta padella), the Mediterranean flour moth (Ephestia kuhniella)* and greater wax moth (*Galleria mellonella).*

Also to be classed with the biting insects are beetles (Coleoptera), for example the granary weevil(*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the floor beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafter (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vineagar fly (*Drosophila melanogaster*), the Mediterranean fruit fly (*Ceratitis capitata*), the house fly (*Musca domestica*), the little house fly (*Fannia canicularis*), the back blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus = Panonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally ticks, such as the relapsing fever tick (*Ornithodorus moubata*).

When applied against pests harmful to health and pests of stored products, particularly flies and mosquitoes, the new products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, or instance by extending the active compounds with conventional pesticide dispersible liquid diluent carrier and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g.

methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chanlk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides or acaricides or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation by the following examples:

EXAMPLE 1

Myzuz test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 1

(Myzus test)

| Active Compound | | Active compound concentration in % | Degree of destruction in % after 1 day |
|---|---|---|---|
| $(CH_3O)_2P(=S)-O-C(CH_3)=N-N$ (cyclic) | (A) | 0.1 | 0 |
| $(C_2H_5O)_2P(=S)-O-C(CH_3)=N-N$ (cyclic) | (B) | 0.1<br>0.01<br>0.001 | 99<br>40<br>0 |
| $(C_2H_5O)(iso-C_3H_7-HN)P(=O)-O-C(=N-N-CH_3)-C(SCH_3)$ | (10) | 0.1<br>0.01<br>0.001 | 100<br>100<br>98 |
| $((CH_3)_2N)(C_2H_5O)P(=O)-O-C(=N-N-CH_3)-C(SCH_3)$ | (1) | 0.1<br>0.01<br>0.001 | 100<br>100<br>60 |
| $(C_2H_5)(C_2H_5O)P(=O)-O-C(=N-N-C_3H_{7iso})-C(S-CH_2-CN)$ | (7) | 0.1<br>0.01 | 100<br>100 |
| $(C_2H_5O)_2P(=O)-O-C(=N-N-CH_3)-C(S-CH_2-CH_2-CN)$ | (3) | 0.1<br>0.01<br>0.001 | 100<br>100<br>98 |
| $(C_2H_5O)_2P(=O)-O-C(=N-N-CH_3)-C(S-CH_2-CH=CH_2)$ | (5) | 0.1<br>0.01<br>0.001 | 100<br>100<br>100 |
| $(C_2H_5)(C_2H_5O)P(=O)-O-C(=N-N-C_3H_7\text{-}iso)-C(S-CH_2-CH=CH_2)$ | (6) | 0.1<br>0.01<br>0.001 | 100<br>100<br>80 |
| $(C_2H_5O)(iso-C_3H_7-HN)P(=O)-O-C(=N-N-C_3H_7\text{-}iso)-C(S-CH_2-CH=CH_2)$ | (8) | 0.1<br>0.01<br>0.001 | 100<br>100<br>50 |
| $(C_2H_5O)_2P(=O)-O-C(=N-N-CH_3)-C(S-CH_2-CH=CH-CH_3)$ | (4) | 0.1<br>0.01<br>0.001 | 100<br>100<br>95 |

EXAMPLE 2

Doralis test (systemic action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were watered with the preparation of the active compound so that the preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following table:

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Table 2

(*Doralis* test/systemic action)

| Active compound | | Active compound concentration in % | Degree of destruction in % after 4 days |
|---|---|---|---|
| (structure with $CH_3O$, $P=S$, $CH_3O$, O, N-N, $CH_3$) | (A) | 0.1 | 0 |
| (structure with $C_2H_5O$, $P=S$, phenyl, O, N-N-$C_3H_7$-i, S-$CH_3$) | (C) | 0.1 | 0 |
| (structure with $C_2H_5O$, P=O, iso-$C_3H_7$-HN, O, N-N-$CH_3$, $SCH_3$) | (10) | 0.1 | 100 |
| (structure with $(CH_3)_2N$, P=O, $C_2H_5O$, O, N-N-$CH_3$, $SCH_3$) | (1) | 0.1 | 100 |
| (structure with $(CH_3)_2N$, P=O, $C_2H_5O$, O, N-N-$C_3H_7$-iso, S-$CH_2$-CN) | (9) | 0.1 | 100 |
| (structure with $C_2H_5O$, P=O, $C_2H_5O$, O, N-N-$CH_3$, S-$CH_2$-$CH_2$-CN) | (3) | 0.1 | 100 |
| (structure with $C_2H_5O$, P=O, $C_2H_5O$, O, N-N-$CH_3$, S-$CH_2$-CH=$CH_2$) | (5) | 0.1 | 100 |
| (structure with $C_2H_5$, P=O, $C_2H_5O$, O, N-N-$C_3H_7$-iso, S-$CH_2$-CH=$CH_2$) | (6) | 0.1 | 100 |
| (structure with $C_2H_5O$, P=O, iso-$C_3H_7$-HN, O, N-N-$C_3H_7$-iso, S-$CH_2$-CH=$CH_2$) | (8) | 0.1 | 100 |
| (structure with $(CH_3)_2N$, P=O, $C_2H_5O$, O, N-N-$C_3H_7$-iso, S-$CH_2$-CH=$CH_2$) | (2) | 0.1 | 100 |

Bean plants (*Phaseolus vulgaris*), which had a height of approximately 10-30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites werre killed, whereas 0% means that none of the spider mites were killed.

The active compounds, the concentrations of the active compounds, the evaluation imes and the results can be seen from the following table.

To produce a suitable preparation of active compound, 30 parts by weight of the active compound in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approximately 2 cm³ of horse muscle. 0.5 ml of the preparation of active compound was applied to this horse meat. After 24 hours, the degree of destruction in % was determined. 100% means that all the larvae had been killed and 0% means that no larvae had been killed.

Table 3

(*Tetranychus* test/resistant)

| Active compound | | Active compound concentration in % | Degree of destruction in % after 2 days |
|---|---|---|---|
| $(CH_3O)_2P(S)-O-C(CH_3)=N-N$ (pyrazole) | (A) | 0.1 | 0 |
| $C_2H_5O, isoC_3H_7-HN, P(O)-O-C(SCH_3)=N-N-CH_3$ | (10) | 0.1 | 100 |
| $(CH_3)_2N, C_2H_5O, P(O)-O-C(SCH_3)=N-N-CH_3$ | (1) | 0.1 | 98 |
| $C_2H_5, C_2H_5O, P(O)-O-C(S-CH_2-CN)=N-N-C_3H_{7iso}$ | (7) | 0.1 | 100 |
| $C_2H_5O, C_2H_5O, P(O)-O-C(S-CH_2-CH_2-CN)=N-N-CH_3$ | (3) | 0.1 | 100 |
| $C_2H_5O, C_2H_5O, P(O)-O-C(S-CH_2-CH=CH_2)=N-N-CH_3$ | (5) | 0.1 | 100 |
| $C_2H_5, C_2H_5O, P(O)-O-C(S-CH_2-CH=CH_2)=N-N-C_3H_7\text{-iso}$ | (6) | 0.1 | 100 |
| $C_2H_5O, C_2H_5O, P(O)-O-C(S-CH_2-CH=CH-CH_3)=N-N-CH_3$ | (4) | 0.1 | 100 |

EXAMPLE 4

Test with parasitic fly larvae

Solvent: 35 parts by weight of ethylene polyglycol monomethyl ether; 35 parts by weight of nonylphenol polyglycol ether The active compounds investigated, the concentrations of the active compounds used and the results obtained can be seen from the table which follows:

Table 4
(Test with parasitic fly larvae/
Lucilia cuprina res.)

| Active compound | | Active compound concentration in ppm | Degree of destruction in % |
|---|---|---|---|
| 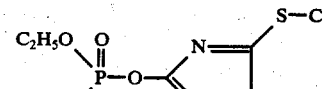 | (3) | 100<br>10 | 100<br>100 |
| 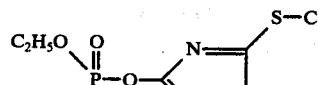 | (4) | 100<br>10<br>1 | 100<br>100<br>100 |
| 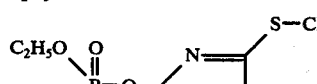 | (5) | 100<br>10<br>1 | 100<br>100<br>>50 |
| 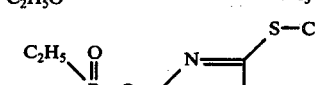 | (7) | 100<br>10 | 100<br>100 |
| 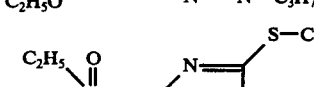 | (6) | 100<br>10<br>1 | 100<br>100<br>>50 |
| 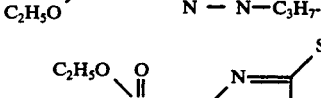 | (8) | 100<br>10<br>1 | 100<br>100<br>100 |
| 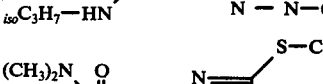 | (2) | 100 | 100 |
| 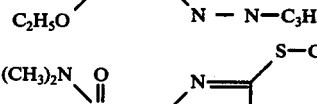 | (9) | 100 | 100 |

The process of this invention is illustrated in the following reparative Examples.

EXAMPLE 5

The hydroxythriazole derivatives (III) used as starting materials were prepared, for example as follows:

(A)

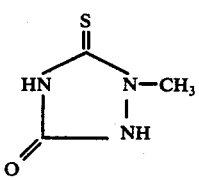

A mixture of 35.4 g (0.2 mole) of compound

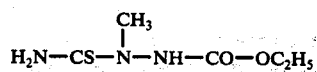

(prepared from methylthiosemicarbazide and pyrocarbonic acid diethyl ester), of melting point 170° C, and 0.2 mole of sodium methylate — dissolved in 100 ml of methanol — was heated under reflux for 5 hours and then evaporated under reduced pressure, and the residue was dissolved in water and reprecipitated with hydrochloric acid. The precipitate was filtered off, dried and recrystallized from methanol. 17 g (65% of theory) of 1-methyl-3-oxo-5-thiatriazolidine-(1,2,4) of melting point 250° C were obtained.

The following could be obtained analogously:

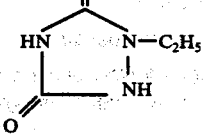

Melting point 222° C
Yield 76% of theory

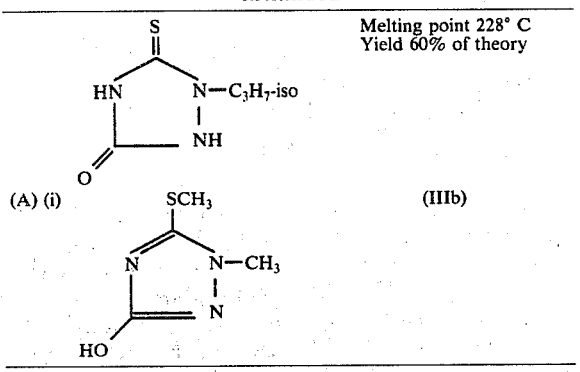

(A) (i)

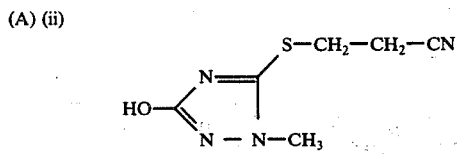

(A) (ii)

13 g of dimethyl sulfate were added dropwise to a mixture of 6 g of potassium hydroxide, 50 ml of water and 13 g (0.1 mole) of the compound as obtained under (A), the reaction solution being at a temperature of 30°–40° C. After the batch had stood for 24 hours at room temperature, it was extracted with methylene chloride. The organic phase was washed and dried and the solvent was distilled off in vacuo. The residue was recrystallized from acetonitrile and 4 g (28% of theory) of 1-methyl-3-hydroxy-5-methylthio-triazole-(1,2,4) of meltingpoint 130°–132° C were obtained.

(IIIc)

1 mole of sodium methylate was added to 131 g (1 mole) of the compound as obtained under (A), 134 g of 2-cyanoethyl bromide were then added at 50°–60° C, the reaction mixture was stirred for a further 3 hours at 60° C and then evaporated, and the residue was triturated with water, filtered off and dried on clay. 105 g (57% of theory) of 1-methyl-3-hydroxy-5-cyanoethylthio-triazole-(1,2,4) of melting point 145°–147° C were obtained.

The following compound were obtained analogously, by reaction with allyl bromide:

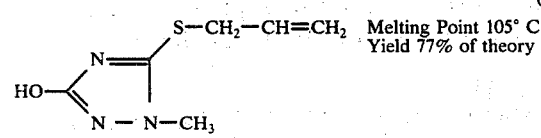
(IIId)

or reaction with 1-bromobutene-(2):

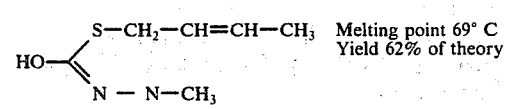
(IIIe)

(B)

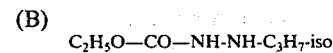

A solution of carbonic acid ethyl hydrazone

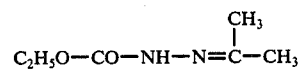

(prepared from carbonic acid ethyl ester hydrazide and acetone) of melting point 70° C, in 500 ml of ethanol, was hydrogenated with 10 g of a 5% strength platinum-on-charcoal catalyst under high pressure at 60° C. The reaction mixture was then filtered, the solvent was evaporated off and the residue was distilled at 87° C/6 mm Hg. 110 g (76% of theory) of N'-isopropyl-carbonic acid ethyl ester hydrazide having a refractive index $n_D^{20}$ of 1.4362 were obtained.

(B) (i)

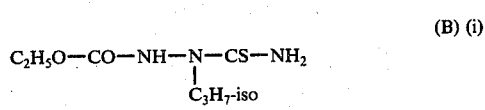

45 ml of concentrated hydrochloric acid, followed by 50 g of potassium thiocyanate, were added to 73 g (0.5 mole) of the product as obtained under (B), in 200 ml of water. The reaction mixture was briefly boiled up and evaporated in a vacuum of 30 mm Hg, and the residue was then heated to 100° C for 2 hours. It was then cooled and recrystallized from water. The product was obtained in 68% yield, and with a melting point of 168° C.

(B) (ii)

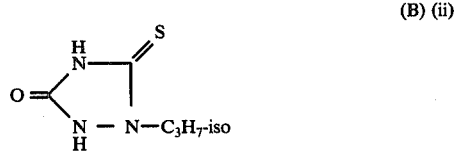

1 mole of sodium methylate solution was added to 205 g (1 mole) of the product as obtained under (B) (i), in 400 ml of methanol, and the reaction solution was boiled for 8 hours under reflux. It was then evaporated and the residue was suspended in a little water. The suspension was acidified with 80 ml of pure concentrated hydrochloric acid and the precipitate was filtered off, washed and recrystallized from methanol. 96 g (60% of theory) of 1-isopropyl-3-oxo-5-thiatriazolidine-(1,2,4) of melting point 228° C were obtained.

(B) (iii) (IIIf)

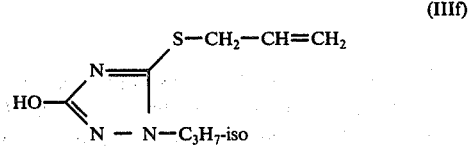

0.5 mole of a sodium methylate solution, followed by 61 g of allyl bromide, was added to 80 g (0.5 mole) of the product as obtained under (B) (ii), in 300 ml of acetonitrile. After stirring for three hours at 50°–60° C, the solvent was evaporated off and the residue was triturated with water and dried on clay. 58 g (59% of theory) of 1-isopropyl-3-hydroxy-5-allylthio-triazole-(1,2,4) of melting point 84°–86° C were obtained.

(C) (IIIg)

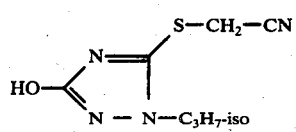

38 g of chloroacetonitrile were added to 80 g (0.5 mole) of the product as obtained under (B) (ii), in 300 ml of acetonitrile, and 75 g of potassium carbonate, and the reaction mixture was stirred for 3 hours at 80° C and cooled. The salt-like solids were filtered off and the solvent was evaporated off. The residue was triturated with water, filtered off and recrystallized from an ethyl acetate: ligroin mixture (11:30). 4 g (4% of theory) of 1-isopropyl-3-hydroxy-5-cyanomethylthiotriazole-(1,2,4) of melting point 61°-62° C were obtained.

EXAMPLE 7

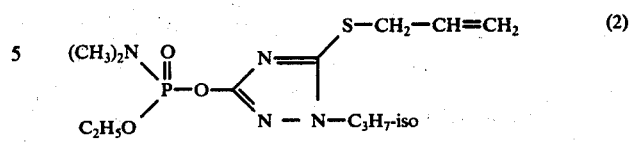

18 g of O-ethyl-N,N-dimethyl-phosphoric acid esteramide chloride were added to a mixture of 20 g (0.1 mole) of 1-isopropyl-3-hydroxy-5-allylmercapto-triazole-(1,2,4) (IIIf) and 15 g of potassium carbonate in 200 ml of acetonitrile and the reaction mixture was stirred at 45°–50° C for 4 hours. It was then poured into water and extracted by shaking with methylene chloride, and after washing and drying the organic phase the solvent was distilled off in vacuo. After "slight distillation" of the residue, 27 g (81% of theory) of O-ethyl-O-[1-isopropyl-5-allylmercapto-triazol(3)yl]-N,N-dimethyl-phosphoric acid diester-amide having a refractive index $n_D^{21}$ of 1.5055 were obtained.

The following compounds could be prepared by methods analogous to either Example 6 or 7:

Table 5

(I)

$$\text{RO} \diagdown \underset{R'}{\overset{O}{\underset{\|}{P}}} - O - \overset{SR'''}{\underset{N - N - R''}{\diagup}}$$

| Compound No. | R | R' | R''' | R'' | Refractive index |
|---|---|---|---|---|---|
| 3 | $-C_2H_5$ | $-OC_2H_5$ | $-CH_2-CH_2-CN$ | $-CH_3$ | $n_D^{23}$: 1.4925 |
| 4 | $-C_2H_5$ | $-OC_2H_5$ | $-CH_2-CH=CH-CH_3$ | $-CH_3$ | $n_D^{23}$: 1.4963 |
| 5 | $-C_2H_5$ | $-OC_2H_5$ | $-CH_2-CH=CH_2$ | $-CH_3$ | $n_D^{21}$: 1.5015 |
| 6 | $-C_2H_5$ | $-C_2H_5$ | $-CH_2-CH=CH_2$ | $-C_3H_7$-iso | $n_D^{21}$: 1.4974 |
| 7 | $-C_2H_5$ | $-C_2H_5$ | $-CH_2-CN$ | $-C_3H_7$-iso | $n_D^{20}$: 1.5008 |
| 8 | $-C_2H_5$ | $-NH-C_3H_7$-iso | $-CH_2-CH=CH_2$ | $-C_3H_7$-iso | $n_D^{21}$: 1.4971 |
| 9 | $-C_2H_5$ | $-N(CH_3)_2$ | $-CH_2-CN$ | $-C_3H_7$-iso | $n_D^{20}$: 1.5076 |
| 10 | $-C_2H_5$ | $-NH-C_3H_7$-iso | $-CH_3$ | $-CH_3$ | $n_D^{22}$: 1.4880 |

EXAMPLE 6

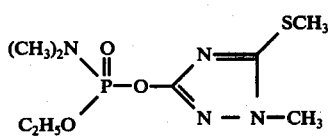

18 g of O-ethyl-N,N-dimethyl-phosphoric acid esteramide chloride were added to a mixture of 15 g (0.1 mole) of 1-methyl-3-hydroxy-5-methylmercapto-triazole-(1,2,4) (IIb) and 15 g of potassium carbonate in 150 ml of acetonitrile and the reaction mixture was stirred at 40°–50° C for 4 hours. The salt-like solids were then filtered off and the solvent was evaporated off in vacuo. The residue was taken up in methylene chloride and after washing and drying the organic phase the solvent was distilled off in vacuo and the residue was subjected to "slight distillation". 16 g (57% of theory) of O-ethyl-O-[1-methyl-5-methylmercapto-triazol-(3)yl]-N,N-dimethyl-phosphoric acid diester-amide having a refractive indedx $n_D^{22}$ of 1.4919 were obtained.

Other compounds which can be similarly prepared and have similar activity include:

O-methyl-O-sec.-butyl-O-[1-butyl-5-vinylmercapto-triazol(3)yl]-phosphoric acid ester,
O-propyl-O-[1-ethyl-5-(4'-cyanobutyl)-mercapto-triazol(3)yl]-butanephosphonic acid ester,
O-sec.-butyl-O-[1-methyl-5-butylmercaptotriazol(3)yl]-N-ethyl-N-butyl-phosphoric acid diester-amide,
O-ethyl-O-[1-methyl-5-(3'-cyanopropyl)-mercapto-triazol(3)yl]-benzenephosphonic acid ester, and the like.

It will be appreciated that the instant specification and examples are set forth by way of illustration and not limitation, and that various modifications and changes may be made without departing from the spirit and scope of the present invention.

What is claimed is:

1. The compound O,O-diethyl-O-[1-methyl-5-(2'-cyanoethyl)-mercapto-triazol(3)yl]-phosphoric acid ester of the formula

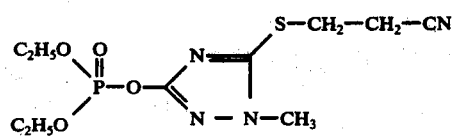

* * * * *